United States Patent
Gündüz et al.

(10) Patent No.: US 8,252,926 B2
(45) Date of Patent: Aug. 28, 2012

(54) PROCESS FOR THE PREPARATION OF IMATINIB BASE

(75) Inventors: Halit Gündüz, Istanbul (TR); Yusuf Özlü, Kocaeli (TR); Serkan Yalçin, Kocaeli (TR)

(73) Assignee: Mustafa Nevzat Ilaç Sanayii A.S., Istanbul (TR)

( * ) Notice: Subject to any disclaimer, the term of this patent is extended or adjusted under 35 U.S.C. 154(b) by 0 days.

(21) Appl. No.: 13/117,309

(22) Filed: May 27, 2011

(65) Prior Publication Data

US 2012/0046463 A1 Feb. 23, 2012

(30) Foreign Application Priority Data

Aug. 23, 2010 (TR) .................................. 2010 07005

(51) Int. Cl.
*C07D 401/14* (2006.01)
(52) U.S. Cl. ....................................................... 544/295
(58) Field of Classification Search .................... 544/295
See application file for complete search history.

(56) References Cited

U.S. PATENT DOCUMENTS 5,521,184 A 5/1996 Zimmermann
7,674,901 B2 3/2010 Szczepek et al.

FOREIGN PATENT DOCUMENTS

| EP | 0 564 409 | 10/1993 |
| WO | WO 99/03854 | 1/1999 |
| WO | WO 03/066613 | 8/2003 |
| WO | WO 2004/074502 | 9/2004 |
| WO | WO 2004/108699 | 12/2004 |

OTHER PUBLICATIONS

Smith et al., March's Advanced Organic Chemistry Reactions, Mechanisms, and Structure, Fifth Edition, 2001, John Wiley & Sons, Inc., pp. 506 and 507.*

* cited by examiner

*Primary Examiner* — Kristin Bianchi
(74) *Attorney, Agent, or Firm* — Wilson Sonsini Goodrich & Rosati

(57) ABSTRACT

Provided is an environmentally-friendly process for preparing imatinib base in high yield, without the use of an organic solvent.

16 Claims, 2 Drawing Sheets

PROCESS FOR THE PREPARATION OF IMATINIB BASE

CROSS-REFERENCE TO RELATED APPLICATIONS

This application claims the benefit of Turkish Patent Application No. TR 2010/07005, filed on Aug. 23, 2010, the contents of which are herein incorporated by reference in their entirety.

FIELD OF THE INVENTION

The invention relates to an environmentally-friendly process for preparing imatinib base in high yield, without the use of an organic solvent.

BACKGROUND OF THE INVENTION

Imatinib base has the chemical name 4-[(4-methylpiperazin-1-yl)methyl]-N[4-methyl-3-[(4-pyridin-3-ylpyrimidin-2-yl)amino]phenyl]benzamide and the following chemical structure.

Imatinib Base (I)

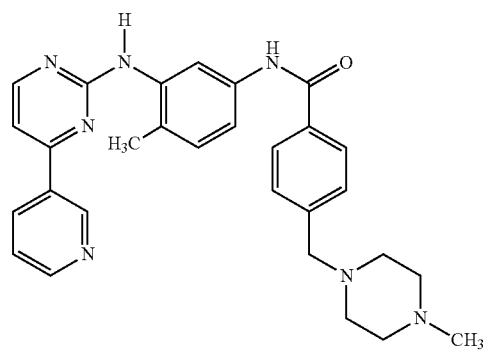

Imatinib is marketed by Novartis as tablets of imatinib mesylate salt under the tradename Gleevec®. Gleevec® has been approved for the treatment of Philadelphia chromosome positive chronic myeloid leukemia (Ph+CML), myelodysplastic/myeloproliferative diseases associated with platelet-derived growth factor receptor gene re-arrangements, aggressive systemic mastocytosis, hypereosinophilic syndrome, chronic eosinophilic leukemia, dermatofibrosarcoma protuberans, and malignant gastrointestinal stromal tumors.

U.S. Pat. No. 5,521,184 ("'184 patent"), also published as EP 0 564 409, describes the synthesis of imatinib base by taking up N-(5-amino-2-methylphenyl)-4-(3-pyridyl)-2-pyrimidine-amine (II) and 4-(4-methylpiperazin-1-yl-methyl) benzoyl chloride (III) in pyridine and stifling the resulting solution under nitrogen at room temperature for 23 hours. (See '184 patent, col. 25, 11. 55-62 (example 21)). The resulting crude imatinib base (I) was then purified by column chromatography using methylene chloride:methanol:25% aqueous ammonia solution (95:5:1). (See id.). International Publication WO 99/03854 ("WO '854") describes the synthesis of imatinib mesylate salt from imatinib freebase prepared by the process of the '184 patent. (See WO '854, pp. 18-19 (Example 1)). The process is illustrated in Scheme 1.

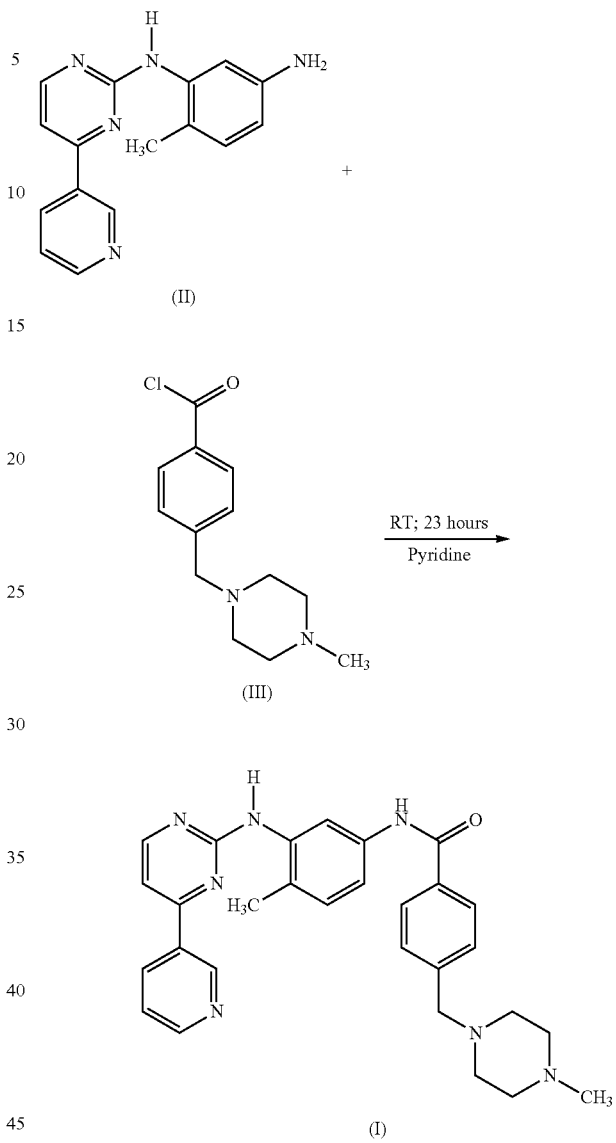

International Publication No. WO 2004/074502 ("WO '502") analyzed the process of the '184 patent, and stated that it was unsatisfactory because, for example, the process was slow, gave rise to undesirable side products, involved tedious work up procedures, and produced low yield of imatinib base. (See WO '502, p. 2). WO '502 further states that use of pyridine as a reaction solvent was undesirable because it was difficult to remove residual traces of pyridine from the final product. (See id.).

WO '502 describes the synthesis of imatinib base by (i) reacting N-(2-methyl-5-aminophenyl-4-(3-pyridyl)-2-pyrimidine-amine (II) and 4-(4-methylpiperazin-1-yl-methyl) benzoyl chloride dihydrochloride (IIIa) in dimethyl formamide ("DMF") at 70° C. for 15 hours to produce imatinib trihydrochloride monohydrate (Ia). The imatinib trihydrochloride monohydrate (Ia) is isolated from the reaction mixture by filtration and then basified in aqueous ammonia to produce imatinib free base (I). (See id. at pp. 17-18 (Examples 1 and 2)). This process is illustrated in Scheme 2.

Scheme 2. Synthesis of Imatinib Base According to WO '502

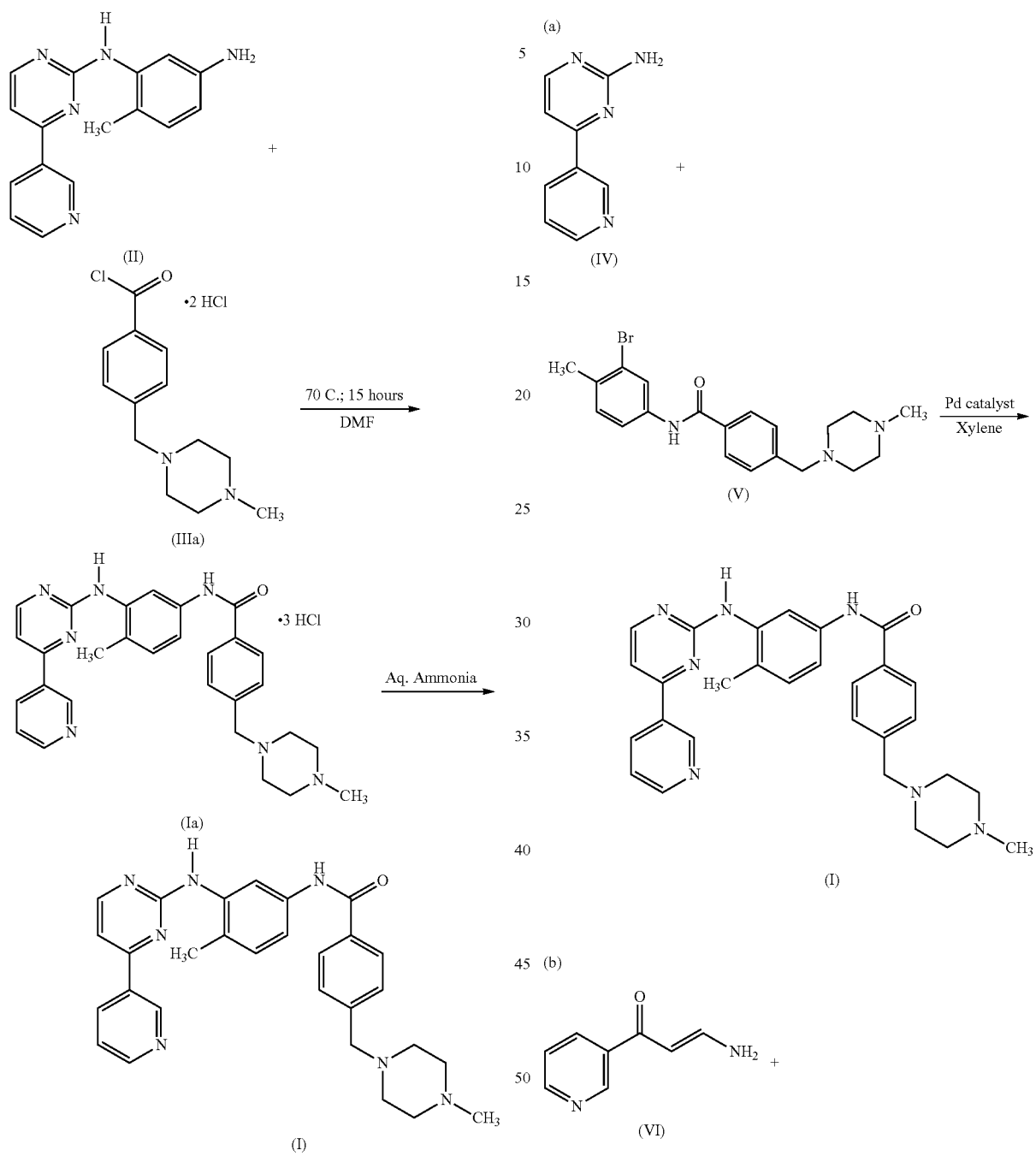

Scheme 3. Synthesis of Imatinib Base According to WO '613

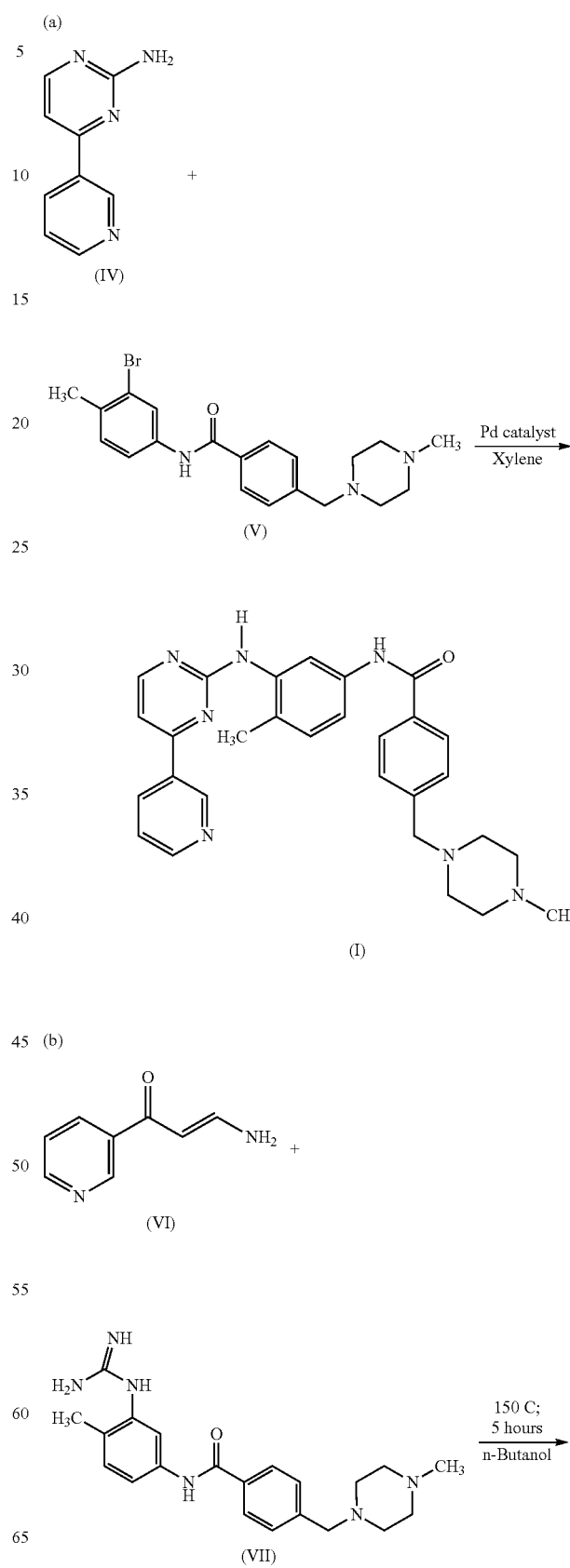

International Publication No. WO 2003/066613 ("WO '613") describes the synthesis of imatinib base by condensing 4-(3-pyridyl)-2-pyrimidine-amine (IV) and N-(3-bromo-4-methyl-phenyl)-4-(4-methyl-piperazin-1-ylmethyl)-benzamide (V) in the presence of a palladium catalyst in xylene under argon. (See WO '613, pp. 20-21 (Example 10)). WO '613 also describes the synthesis of imatinib base by the reaction of 3-amino-1-pyridin-3-yl-propenone (VI) and N-(3-guanidino-4-methylphenyl)-4-(4-methylpiperazin-1-ylmethyl)-benzamide (VII) in n-butanol at 150° C. for 5 hours. (See id. at p. 21 (Example 9)). These processes are illustrated in Scheme 3.

-continued (I)

The methods described in WO '613 are also unsatisfactory for industrial scale production. Use of palladium catalyst is expensive, and toxic. Also use of high temperatures and inert atmosphere make these methods expensive and problematic for bulk scale productions.

International Publication No. WO 2004/108699 ("WO '699") and U.S. Pat. No. 7,674,901 ("'901 patent") disclose the synthesis of imatinib base by condensation of N-(2-methyl-5-aminophenyl-4-(3-pyridyl)-2-pyrimidine-amine (II) with 4-chloromethylbenzoyl chloride (VIII) in the presence of triethylamine in an organic solvent to form 4-(chloromethyl N-(4-methyl-3-[(4-3-pyridyl-2-pyrimidine]-amino) phenyl benzamide (IX), which is then reacted with N-methylpiperazine in an organic solvent to form imatinib base. (See WO '699, pp. 21-22 (Example 1); '901 patent, col. 16, l. 17 to col. 17, l. 32).

Scheme 4. Synthesis of Imatinib Base According to WO '699 and the '901 Patent

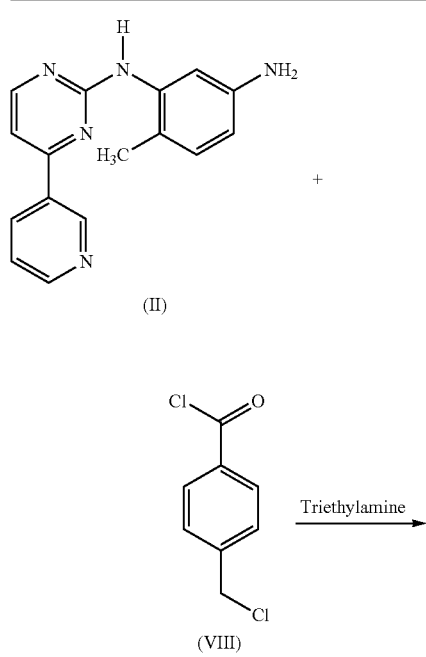

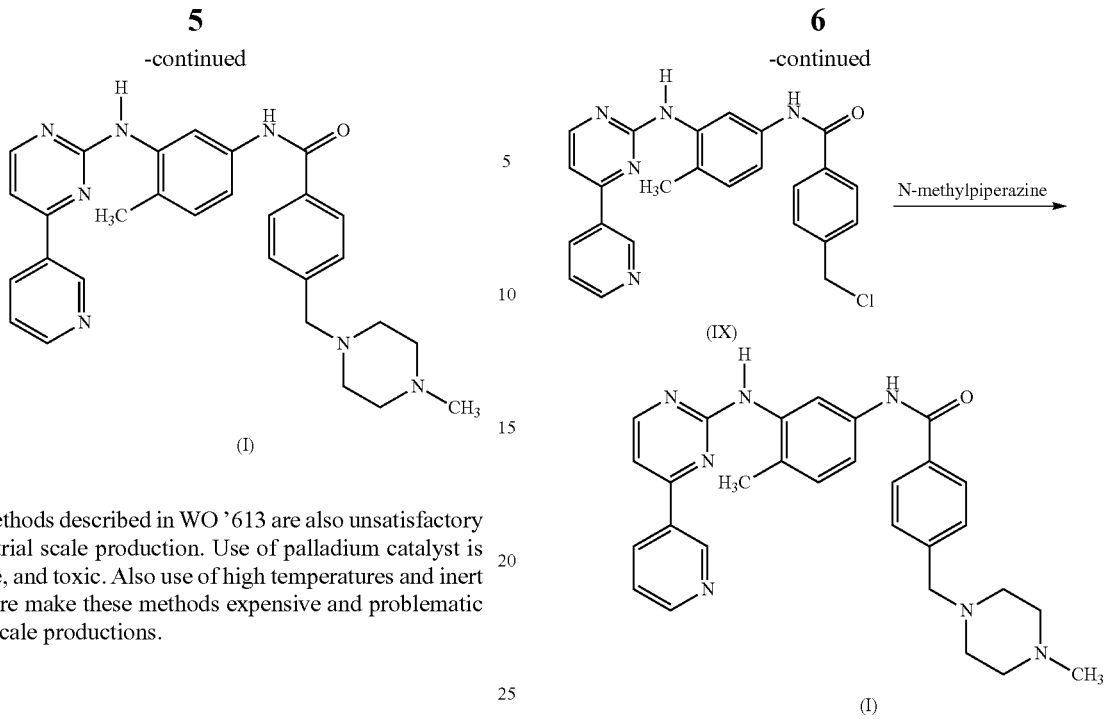

The methods described in WO '699 are also unsatisfactory for industrial scale production in view of the use of organic bases, such as triethyl amine, and organic solvents, such as chloroform and DMF, which may be difficult to remove from the final imatinib base product.

Accordingly, there is a need in the art for additional processes for synthesizing imatinib base that are suitable for use on an industrial scale.

SUMMARY OF THE INVENTION

In one embodiment, the invention encompasses processes for preparing imatinib base comprising: (a) condensing N-(2-methyl-5-aminophenyl-4-(3-pyridyl)-2-pyrimidine-amine and 4-(4-methylpiperazin-1-yl-methyl)benzoyl chloride dihydrochloride in the presence of a solvent to obtain imatinib hydrochloride; and (b) combining the imatinib hydrochloride with a base to obtain imatinib base, wherein the solvent is not an organic solvent.

In another embodiment, the invention encompasses processes for preparing imatinib mesylate comprising: (a) condensing N-(2-methyl-5-aminophenyl-4-(3-pyridyl)-2-pyrimidine-amine and 4-(4-methylpiperazin-1-yl-methyl) benzoyl chloride dihydrochloride in the presence of a solvent to obtain imatinib hydrochloride; (b) combining the imatinib hydrochloride with a base to obtain imatinib base; and (c) combining the imatinib base with methanesulfonic acid to obtain imatinib mesylate, wherein the solvent is not an organic solvent.

DETAILED DESCRIPTION OF THE INVENTION

Figure 1:
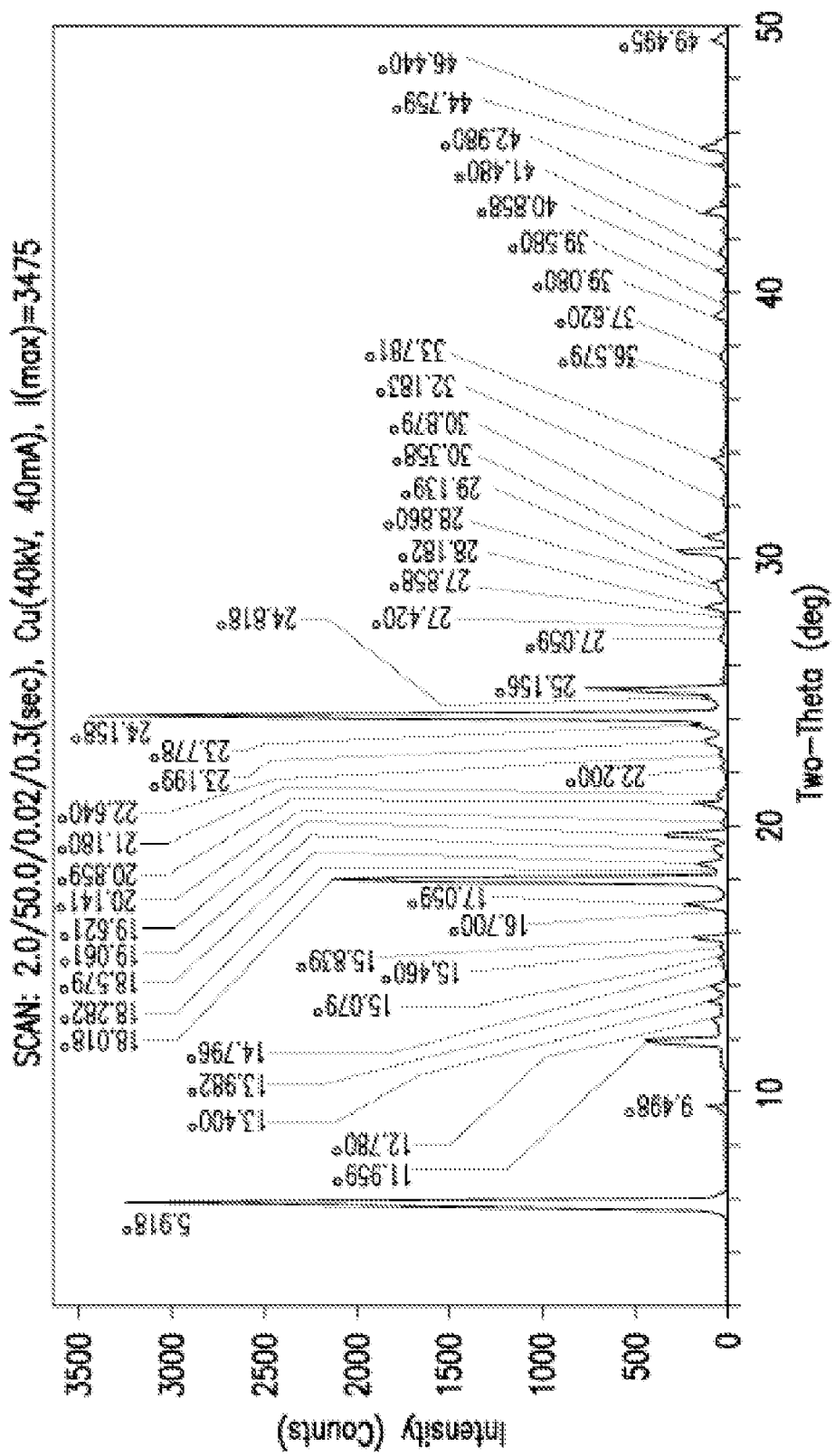
FIG. 1 shows the powder X-ray diffraction pattern of the imatinib base (I) prepared according to Example 2.

The present invention provides an improved process for preparing imatinib base in high yields in the absence of organic solvent. Organic solvents include, but are not limited to, DMF, pyridine, chloroform, N,N-dimethylacetamide ("DMACT"), N-methylpyrrolidone ("NMP"), dioxane, sulfolane, diglyme, toluene, dichloromethane, dimethyl sulfoxide ("DMSO"), tetrahydrofuran ("THF") and triethyl amine.

In one embodiment, the invention encompasses a process for preparing imatinib base (I) comprising condensing N-(2-methyl-5-aminophenyl-4-(3-pyridyl)-2-pyrimidine-amine (II) and 4-(4-methylpiperazin-1-yl-methyl)benzoyl chloride dihydrochloride (IIIa) in the absence of an organic solvent. This process is depicted in Scheme 5.

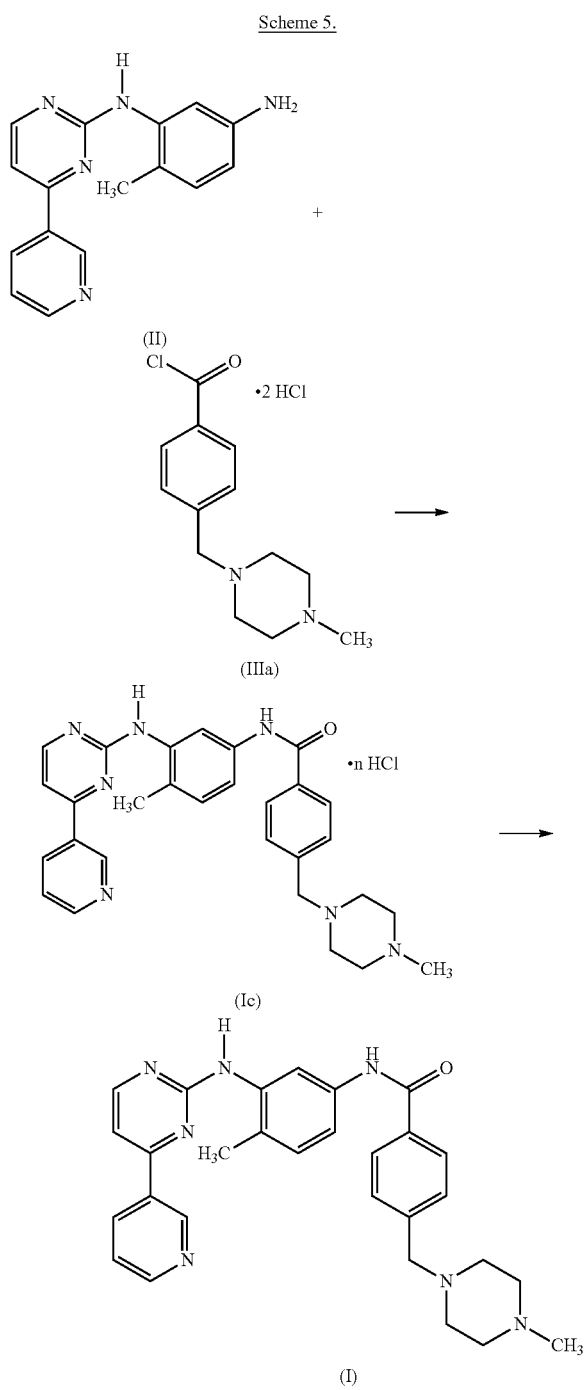

Compound (II) and compound (IIIa) can be obtained commercially or prepared by one of skill in the art according to known procedures.

Compound (II) and compound (IIIa) are typically combined in a molar ratio of about 1:1 to about 1:2.5. In one embodiment, compound (II) and compound (IIIa) are combined in a molar ratio of about 1:1. Preferably, compound (IIIa) is present in excess, which can increase the yield of imatinib base. In one embodiment, compound (II) and compound (IIIa) are combined in a molar ratio of about 1:1.05 to about 1:2.5, about 1:1.25 to about 1:2.25, or about 1:1.5 to about 1:2.

Compound (II) and compound (IIIa) are typically combined in the presence of a solvent or mixture of solvents. Suitable solvents include, but are not limited to, water and aqueous-based mixtures, such as aqueous pyridine, aqueous DMF, aqueous DMACT, aqueous DMSO, aqueous triethyl amine, aqueous THF, aqueous dioxane, or aqueous ammonia, and mixtures thereof. In one embodiment, the solvent is water. Typically, the solvent is present in an amount of about 10 ml to about 30 ml per gram of starting material (i.e., compound (II)).

In one embodiment, the solvent is not an organic solvent. In another embodiment, the solvent is substantially free of organic solvent. The solvent may contain less than 50%, less than 40%, less than 30%, less than 20%, less than 10%, less than 5%, or less than 1% organic solvent by volume.

The condensation of compound (II) and compound (Ma) can be performed at a temperature of about −5° C. to about 30° C. In one embodiment, the condensation is performed at a temperature of about −5° C. to about 20° C., about −5° C. to about 10° C., about 0° C. to about 25° C., about 0° C. to about 10° C., about 0° C. to about 5° C., or about 5° C. to about 10° C. Highest yields of imatinib base are typically observed when the condensation reaction is performed at a temperature of about 0° C. to about 5° C.

In one embodiment, compound (II) and solvent are combined to form a mixture, and compound (IIIa) is added to the mixture in portions. Not to be limited by theory, it is believed that adding compound (IIIa) to the mixture in portions avoids reaction of compound (IIIa) with the water solvent to form the undesired corresponding carboxylic acid compound, 4-(4-methylpiperazin-1-yl-methyl)benzoic acid. The amounts of the portions and addition times may vary. In one embodiment, compound (IIIa) is added to the mixture in portions of about 4% to about 8%, about 5% to about 7%, or about 6% of the total amount of compound (IIIa) to be added to the mixture. In one embodiment, compound (IIIa) is added to the mixture in portions over about 1 to about 3 hours or about 2 to about 3 hours. The mixture can be stirred during the course of the addition of compound (IIIa).

Typically, the condensation is complete shortly after addition of the last portion of compound (IIIa). In one embodiment, the mixture of compound (II), compound (IIIa), and solvent is maintained for about 30 minutes after the last portion of compound (IIIa) is added. The mixture can be maintained with stirring.

The progress of the condensation can be monitored by high performance liquid chromatography ("HPLC"), thin layer chromatography ("TLC"), or any other technique known to one of skill in the art. In one embodiment, progress of the condensation is monitored by HPLC. Progress of the condensation can be determined by consumption of compound (II), and the condensation is deemed complete once all compound (II) is consumed. If the condensation does not progress to completion, additional amounts of compound (IIIa) can be added portion-wise until all compound (II) is consumed.

Optionally, upon completion of the condensation, the reaction mixture is filtered, for example over a Celite bed, to remove any unreacted starting materials and other insoluble particles.

The imatinib hydrochloride (Ic) thus produced by the condensation of compound (II) and compound (IIIa) can be converted in situ to imatinib base (I), without isolation from the reaction mixture. In one embodiment, the imatinib hydrochloride (Ic) is converted to imatinib base (I) by addition of a base to the reaction mixture. The base can be an organic or an inorganic base. Suitable bases include, but are not limited to, alkali metal hydroxides, such as sodium hydroxide, and potassium hydroxide, ammonium hydroxide, alkali metal carbonates, such as sodium carbonate and potassium carbonate, and alkali metal bicarbonates, such as sodium bicarbonate and potassium bicarbonate. In one embodiment, the base is added in an amount sufficient to adjust the pH of the reaction mixture to greater than 7, about 7.5 to about 13.5, about 8 to about 12, or about 9 or about 10. In one embodiment, the reaction mixture is maintained at a temperature of above 25° C. during addition of the base. In another embodiment, the reaction mixture is obtained at a temperature of about 30° C. to about 65° C., about 40° C. to about 60° C., or about 50° C. to about 55° C.

The imatinib base (I) typically precipitates from the reaction mixture at basic pH. The precipitated imatinib base (I) can be amorphous or crystalline. It has been found that maintaining the reaction mixture at higher temperatures during addition of the base favors precipitation of crystalline imatinib base (I), while maintaining the reaction mixture at lower temperatures during addition of the base favors precipitation of amorphous imatinib base (I).

The precipitated imatinib base (I) can be isolated from the reaction mixture by filtration or any other technique known to one of skill in the art.

Typically, the imatinib base (I) is isolated in a yield of greater than 85%. In one embodiment, the imatinib base (I) is isolated in a yield of about 90% to about 99%, about 95% to about 99%, about 98% to about 99%, or about 98%.

Not to be limited by theory, the low water solubility of compound (II) and imatinib base (I) is believed to contribute to the high yields of imatinib base (I) observed with the process of the invention. Low water solubility of compound (II) prevents reaction of compound (II) with the water solvent to form unwanted side products during the condensation. Low water solubility of imatinib base (I) facilitates precipitation of the imatinib base from the reaction mixture so that it can be readily isolated. Further, the process of the invention uses milder conditions (for example, lower temperatures, shorter reaction times, absence of catalyst) than the prior art processes, which is also believed to contribute to the high yield of imatinib base (I).

In one embodiment, the imatinib base (I) is isolated in a purity of greater than 85% by weight. In another embodiment, the imatinib base (I) is isolated in a purity of about 90% to about 99%, about 95% to about 99%, about 98% to about 99%, or about 98% by weight. Purity of the imatinib base (I) can be measured by any technique known to one of skill in the art, for example, by HPLC.

Optionally, the isolated imatinib base (I) can be further purified by any technique known to one of skill in the art. In one embodiment, the imatinib base (I) is purified by recrystallization from a suitable solvent. Suitable solvents include, but are not limited to, alcohols, such as $C_1$-$C_6$ linear or branched alcohols including methyl alcohol, ethyl alcohol, propyl alcohol, isopropyl alcohol, and t-butyl alcohol. In one embodiment, the imatinib base (I) is recrystallized from ethyl alcohol or isopropyl alcohol. The imatinib base (I) can be recrystallized once or twice. In one embodiment, the recrystallized imatinib base (I) has a purity of greater than 95% by weight. In another embodiment, the recrystallized imatinib base (I) has a purity of about 95% to about 99%, about 98% to about 99%, or about 99% by weight.

The imatinib base (I) prepared by the process of the invention, with or without recrystallization, can further be used to prepare any salt of imatinib, such as imatinib mesylate (Ib). Imatinib mesylate (Ib) can be prepared from imatinib base (I) by any method known to one of skill in the art, for example, such as the method described in WO '854, herein incorporated by reference. In one embodiment, imatinib mesylate (Ib) is prepared by combining imatinib base (I) with methanesulfonic acid.

The process of the invention as described above has several advantages over the prior art methods, including but not limited to: ease of industrial applicability; high yield of imatinib base; high purity of imatinib base; use of environmentally-friendly solvents; reduced costs in handling/storing/disposing of solvents used in the process.

Having described the invention with reference to certain embodiments, other embodiments will become apparent to one skilled in the art from consideration of the specification. The invention is further defined by reference to the following examples. It will be apparent to those skilled in the art that many modifications, both to materials and methods, may be practiced without departing from the scope of the invention.

EXAMPLES

Example 1

Synthesis of Imatinib Base (I)

N-(5-Amino-2-methylphenyl)-4-(3-pyridyl)-2-pirimidine-amine (II, 15 g; 54.09 mmole) and process water (350 g) were added to a round bottom flask to form a mixture. The temperature of the mixture was adjusted to between 0° C. to 5° C. At this temperature, 4-(4-methylpiperazin-1-yl-methyl) benzoyl chloride di-hydrochloride (Ma, 34 g; 104.41 mmol) was added to the mixture in 17 portions of 2 g, one portion added to the mixture every 10 minutes. The progress of the reaction was monitored by HPLC and the reaction was carried out until the N-(5-Amino-2-methylphenyl)-4-(3-pyridyl)-2-pirimidine-amine (II) was completely consumed.

After completion of the reaction, activated charcoal (3.5 g) was added to the reaction mixture and the reaction mixture was stirred with the activated charcoal for 15 minutes. The reaction mixture was then filtered over a bed of celite. The filter bed was washed with process water (30 g).

The filtrate was then heated to a temperature of between 50° C. to 55° C. At this temperature, the pH of the filtrate was adjusted to a value of between 9 and 9.5 by the addition of 20% NaOH. The resulting precipitated imatinib base (I) was then filtered under vacuum. The isolated, crude imatinib base (I) was then washed with additional process water (30 g) and kept under vacuum for an additional 30 minutes. The crude imatinib base (I) was then dried in a vacuum oven at 60° C.

Yield of crude imatinib base (I)=26.5 g (53.69 mmol; 99.26%); Purity of crude imatinib base (I)=98.2% by weight.

Example 2

Purification of Imatinib Base (I)

Crude Imatinib base (I) (26.5 g; 53.69 mmole) and ethyl alcohol (320 g) were taken up in a round bottom flask to form a mixture. The mixture was then heated to reflux until the imatinib base (I) was completely dissolved in the ethyl alcohol.

After dissolution, the mixture was cooled to a temperature of 55° C. to 60° C., and activated charcoal was added (3.5 g) and stirred for 15 minutes. The mixture was then filtered over a celite bed while hot and the filter was washed with hot ethyl alcohol (20 g).

The filtrate was allowed to cool while stirred for 2 hours. Once the filtrate reached a temperature of below 50° C., a precipitate began to form. In order to increase the amount of precipitation, the mixture was further cooled to a temperature of −5° C. to 0° C. and stirred for five hours at this temperature. The resulting precipitated imatinib base (I) was isolated via vacuum filtration and washed with cold ethanol. The isolated, purified imatinib base (I) was kept under vacuum for 30 minutes followed by drying at 60° C.

Yield of purified imatinib base (I)=23 g (46.60 mmol; 86.79%); Yield of purified imatinib base (I)=99.5% by weight.

Figure 2:
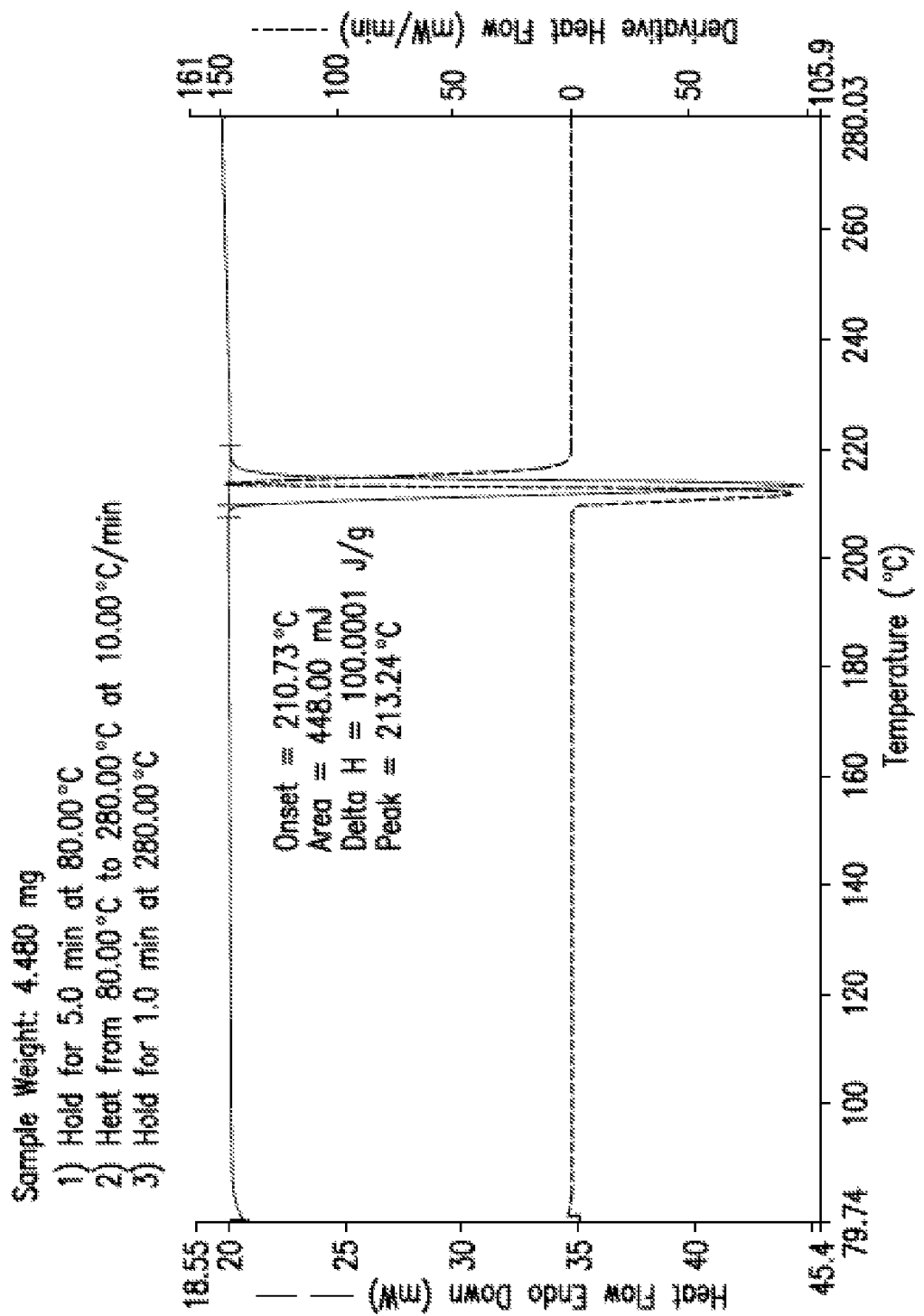
FIG. 2 shows the differential scanning calorimetry trace of the imatinib base (I) prepared according to Example 2.

The purified imatinib base (I) was analyzed by powder X-ray diffraction ("PXRD") and differential scanning calorimetry ("DSC"). The PXRD pattern is shown in FIG. 1. As shown in FIG. 1, in one embodiment, the imatinib base (I) has a PXRD pattern with peaks at 5.9, 12.0, 17.1, 18.0, 18.6, 19.6, 20.9, 23.8, 24.2, and 25.2±0.2 degrees 2θ. The DSC trace is shown in FIG. 2. As shown in FIG. 2, the imatinib base (I) exhibits a peak onset at 210° C.

Example 3

HPLC Method for Measuring Purity of Imatinib Base (I)

The purity of imatinib base (I) in Examples 1 and 2 above was measured by HPLC using a Waters Symmetry Shield RP18, 150×4.6 mm, 5.0 micron column at a column temperature of 40° C. and a flow rate of 1.0 ml/min, and detection at 237 nm.

The mobile phase was prepared by dissolving 0.68 grams of potassium dihydrogen phosphate and 3.25 grams of 1-octanesulfonic acid sodium salt in 500 ml of water. The pH of the resulting solution was then adjusted to 4.0 with 10% (v/v) phosphoric acid. A 420 ml portion of this solution was then combined with 580 ml methanol, filtered and used as the mobile phase.

Example 4

Scale-Up Synthesis of Imatinib Base (I)

The procedure set forth in Example 1 was scaled-up and validated at a batch size of 30 kg N-(5-Amino-2-methylphenyl)-4-(3-pyridyl)-2-pirimidine-amine (II) as follows:

(a) Preparation of Imatinib Base (I)

Process water (700 kg) and N-(5-amino-2-methylphenyl)-4-(3-pyridyl)-2-pyrimidine-amine (II, 30 kg) were charged into a reactor to form a mixture. The temperature of the mixture was adjusted to between 0° C. to 5° C. At this temperature, 4-(4-methylpiperazin-1-yl-methyl)benzoyl chloride di-hydrochloride (IIIa, 68 kg) was added to the mixture in 17 portions of 4 kg, one portion added to the mixture every 10 minutes.

After completion of the reaction, activated charcoal (3.5 kg) was added to the reaction mixture and the reaction mixture was stirred with the activated charcoal for 15 minutes. The reaction mixture was then filtered over a bed of celite. The filter bed was washed with process water (60 kg).

The filtrate was then heated to a temperature of between 50° C. to 55° C. At this temperature, the pH of the filtrate was adjusted to a value of between 9 and 9.5 by the addition of 20% NaOH. The resulting precipitated imatinib base (I) was then centrifuged under vacuum. The isolated, crude imatinib base (I) was then washed with additional process water (60 kg) and kept under vacuum for an additional 30 minutes. The crude imatinib base (I) was then dried in a vacuum oven at 60° C.

(b) Purification of Imatinib Base (I)

The crude Imatinib base (I) prepared according to step (a) and ethyl alcohol (640 kg) were charged into a reactor to form a mixture. The mixture was then heated to reflux until the imatinib base (I) was completely dissolved in the ethyl alcohol.

After dissolution, the mixture was cooled to a temperature of 55° C. to 60° C., and activated charcoal was added (3.5 kg) and stirred for 15 minutes. The mixture was then filtered over a celite bed while hot and the filter was washed with hot ethyl alcohol (40 kg).

The filtrate was allowed to cool while stirred for 2 hours. The mixture was then further cooled to a temperature of −5° C. to 0° C. and stirred for five hours at this temperature. The resulting precipitated imatinib base (I) was then centrifuged under vacuum and washed with cold ethanol. The isolated, purified imatinib base (I) was kept under vacuum for 30 minutes followed by drying at 60° C.

The results of the validation batches are presented in the Table below:

| Batch | Starting Material (II) (kg) | Product (I) (kg) | Purity (% by weight) |
|---|---|---|---|
| 1 | 30 | 43.8 | 99.3 |
| 2 | 30 | 45.9 | 99.8 |
| 3 | 30 | 48.5 | 100.0 |

We claim:

1. A process for preparing imatinib base comprising:
   (a) condensing N-(2-methyl-5-aminophenyl-4-(3-pyridyl)-2-pyrimidine-amine and 4-(4-methylpiperazin-1-yl-methyl)benzoyl chloride dihydrochloride in the presence of a solvent to obtain imatinib hydrochloride; and
   (b) combining the imatinib hydrochloride with a base to obtain imatinib base, wherein the solvent is not an organic solvent, and
   wherein the base is an alkali metal hydroxide, alkali metal carbonate, or alkali metal bicarbonate.

2. The process of claim 1, wherein the 4-(4-methylpiperazin-1-yl-methyl)benzoyl chloride dihydrochloride is present in a molar excess compared to the N-(2-methyl-5-aminophenyl-4-(3-pyridyl)-2-pyrimidine-amine.

3. The process of claim 1, wherein the N-(2-methyl-5-aminophenyl-4-(3-pyridyl)-2-pyrimidine-amine and 4-(4-methylpiperazin-1-yl-methyl)benzoyl chloride dihydrochloride are present in a molar ratio of about 1:1.5 to about 1:2.

4. The process of claim 1, wherein the solvent is water.

5. The process of claim 1, wherein the condensation is performed at a temperature of about 0° C. to about 10° C.

6. The process of claim 1, wherein the condensation is performed by:

(i) combining the N-(2-methyl-5-aminophenyl-4-(3-pyridyl)-2-pyrimidine-amine and the solvent to form a mixture; and
(ii) adding the 4-(4-methylpiperazin-1-yl-methyl)benzoyl chloride dihydrochloride portion-wise to the mixture.

7. The process of claim 6, wherein the 4-(4-methylpiperazin-1-yl-methyl)benzoyl chloride dihydrochloride is added to the mixture in portions of about 4% to about 8% over a period of about 2 to about 3 hours.

8. The process of claim 1, wherein the base is an alkali metal hydroxide.

9. The process of claim 1, wherein the base is present in an amount sufficient to achieve a pH of about 9 to about 10.

10. The process of claim 1, wherein the imatinib hydrochloride is combined with the base at a temperature of about 40° C. to about 60° C.

11. The process of claim 1, further comprising isolating the imatinib base.

12. The process of claim 11, wherein the imatinib base is isolated in a yield of about 90% to about 99%.

13. The process of claim 11, wherein the isolated imatinib base has a purity of about 90% to about 99% by weight.

14. The process of claim 11, wherein the imatinib base is isolated in crystalline form.

15. The process of claim 11, further comprising recrystallizing the isolated imatinib base.

16. The process of claim 15, wherein the isolated imatinib base is recrystallized from ethyl alcohol.

* * * * *